(12) United States Patent
Das

(10) Patent No.: US 10,496,791 B2
(45) Date of Patent: Dec. 3, 2019

(54) PROGNOSTICS AND HEALTH MANAGEMENT SYSTEM

(71) Applicant: Lockheed Martin Corporation, Bethesda, MD (US)

(72) Inventor: Sreerupa Das, Oviedo, FL (US)

(73) Assignee: Lockheed Martin Corporation, Bethesda, MD (US)

( * ) Notice: Subject to any disclaimer, the term of this patent is extended or adjusted under 35 U.S.C. 154(b) by 1096 days.

(21) Appl. No.: 14/689,413

(22) Filed: Apr. 17, 2015

(65) Prior Publication Data

US 2015/0302163 A1   Oct. 22, 2015

Related U.S. Application Data

(60) Provisional application No. 61/980,872, filed on Apr. 17, 2014, provisional application No. 62/067,050, filed on Oct. 22, 2014.

(51) Int. Cl.
*G06F 19/00* (2018.01)
*G05B 23/02* (2006.01)
(Continued)

(52) U.S. Cl.
CPC ..... *G06F 19/3418* (2013.01); *G05B 23/0213* (2013.01); *G06N 3/02* (2013.01); *G06N 20/00* (2019.01)

(58) Field of Classification Search
CPC ...... G06F 19/3418; G05B 23/02; G06N 3/02; G01M 5/0033; G01M 5/0066
(Continued)

(56) References Cited

U.S. PATENT DOCUMENTS 6,859,831 B1   2/2005   Gelvin et al.
7,581,434 B1   9/2009   Discenzo et al.
(Continued)

FOREIGN PATENT DOCUMENTS

EP   1935576 A1   6/2008
GB   2514980 A    12/2014
WO   2013155161 A1   10/2013

OTHER PUBLICATIONS

Patent Examination Report No. 1 for Australian Patent Application No. 2013245998, dated Jan. 27, 2016, 3 pages.
(Continued)

*Primary Examiner* — Hiep V Nguyen
(74) *Attorney, Agent, or Firm* — Withrow & Terranova, PLLC

(57) ABSTRACT

A flexible prognostics and health management (PHM) device is disclosed. Sensor data is generated that quantifies real-time conditions of components in a machine based on sensor signals generated by sensors. A PHM system loads a PHM module that implements externally invokable functions. The PHM system receives an analytics script. The analytics script comprises interpretable commands and predictive learning model parameter values associated with a predictive learning model. Some of the interpretable commands are configured to invoke some of the externally invokable functions with at least some of the predictive learning model parameter values. The PHM module invokes a command interpreter module to interpret an interpretable command and the predictive learning model parameter values and generate first executable bytecodes. The first executable bytecodes execute to generate a notification identifying a predicted future condition of a first component for presentation on a display device.

20 Claims, 8 Drawing Sheets

US 10,496,791 B2
Page 2

(51) Int. Cl.
  *G06N 3/02* (2006.01)
  *G06N 20/00* (2019.01)
(58) Field of Classification Search
  USPC .......................................................... 705/2
  See application file for complete search history.

(56) References Cited

U.S. PATENT DOCUMENTS

| | | | |
|---|---|---|---|
| 8,600,685 | B2 | 12/2013 | Kalgren et al. |
| 2002/0133320 | A1 | 9/2002 | Wegerich et al. |
| 2004/0203700 | A1* | 10/2004 | Chan ..................... H04W 84/16 455/421 |
| 2005/0049988 | A1 | 3/2005 | Dahlquist et al. |
| 2005/0273218 | A1 | 12/2005 | Breed et al. |
| 2006/0167659 | A1 | 7/2006 | Miyasaka et al. |
| 2006/0224533 | A1 | 10/2006 | Thaler |
| 2007/0118271 | A1 | 5/2007 | Wiseman et al. |
| 2007/0118333 | A1 | 5/2007 | Miyasaka et al. |
| 2008/0177505 | A1 | 7/2008 | Volponi |
| 2008/0221721 | A1 | 9/2008 | Reed et al. |
| 2009/0204232 | A1* | 8/2009 | Guru ...................... G06Q 10/06 700/9 |
| 2011/0071725 | A1 | 3/2011 | Kleve et al. |
| 2012/0078460 | A1 | 3/2012 | Mortensen |
| 2013/0069792 | A1 | 3/2013 | Blevins et al. |
| 2013/0268241 | A1 | 10/2013 | Das et al. |
| 2014/0358825 | A1* | 12/2014 | Phillipps .............. G06N 99/005 706/11 |

OTHER PUBLICATIONS

First Examination Report for New Zealand Patent Application No. 700767, dated Nov. 26, 2015, 4 pages.
Notice of Allowance for U.S. Appl. No. 14/689,264, dated Jul. 20, 2016, 9 pages.
Notice of Acceptance for Australian Patent Application No. 2013245998, dated Jul. 14, 2016, 2 pages.
Further Examination Report for New Zealand Patent Application No. 700767, dated Aug. 8, 2016, 2 pages.
Non-Final Office Action for U.S. Appl. No. 13/860,051, dated Nov. 3, 2016, 6 pages.
Further Examination Report Postponed Acceptance for New Zealand Patent Application No. 700767, dated Oct. 21, 2016, 1 page.
International Preliminary Report on Patentability for International Patent Application No. PCT/US2015/026331, dated Oct. 27, 2016, 10 pages.
International Preliminary Report on Patentability for International Patent Application No. PCT/US2015/026370, dated Oct. 27, 2016, 9 pages.
Non-Final Office Action for U.S. Appl. No. 13/860,051, dated Apr. 4, 2016, 6 pages.
Non-Final Office Action for U.S. Appl. No. 14/689,264, dated Mar. 2, 2016, 10 pages.
Further Examination Report for New Zealand Patent Application No. 700767, dated Apr. 8, 2016, 3 pages.
Author Unknown, "Condition Based Maintenance Plus (CBM+) for Material Maintenance," Department of Defense Instruction, No. 4151.22, Dec. 2, 2007, 11 pages.
Author Unknown, "Condition Based Maintenance Plus (CBM+) Roadmap," Deputy Chief of Staff, G-4, Headquarters, Department of the Army, Logistics Innovation Agency, Dec. 13, 2007, 88 pages.

Bechtel, Jim, "Architectural Design Challenges for Ground Vehicle CBM+ System of Systems," Presented at Purdue: Systems Integrity for Defense Summit, Mar. 30-31, 2009, West Lafayette, Indiana, TARDEC, 11 pages.
Bergemann, Tobias, "Bytecode," Wikipedia, the free encyclopedia, retrieved from https://en.wikipedia.org/w/index.php?title=Bytecode &oldid=598575789, last edited Mar. 7, 2014, Wikipedia Foundation, 3 pages.
Brown, Edward, R., et al., "Prognostics and Health Management: A Data-Driven Approach to Supporting the F-35 Lightning II," Presented at IEEE Aerospace Conference, Mar. 3-10, 2007, Big Sky, Montana, 12 pages.
Collobert, Ronan, et al., "Implementing Neural Networks Efficiently." In Montavon, G., et al., eds. Neural Networks: Tricks of the Trade, 2nd ed. Lecture Notes in Computer Science, vol. 7700, 2012, Springer-Verlag Berlin Heidelberg, pp. 537-557.
Das, Sreerupa, "An Efficient Way to Enable Prognostics in an Onboard System," IEEE Aerospace Conference, Mar. 7-14, 2015, Big Sky, Montana, IEEE, pp. 1-7.
Das, Sreerupa, et al., "Essential Steps in Prognostic Health Management," Presented at IEEE International Conference on Prognostics and Health Management, Jun. 20-23, 2011, Montreal, Quebec, Canada, 9 pages.
Gorsich, David, et al., "Ground Vehicle Condition Based Maintenance," Presented at NATO AVT172 CBM Workshop, Bucharest, Romania, Oct. 4-8, 2010, TACOM/TARDEC, 39 pages.
Grantner, Janos, et al., "Condition Based Maintenance for Light Trucks," Presented at IEEE International Conference on Systems, Man, and Cybernetics, Oct. 10-13, 2010, Istanbul, Turkey, 9 pages.
McCollom, Neal, N., et al., "PHM on the F-35 Fighter," Presented at IEEE Conference on Prognostics and Health Management, Jun. 20-23, 2011, Montreal, Quebec, Canada, 10 pages.
Rabeno, Eric, et al., "Condition Based Maintenance of Military Ground Vehicles," Presented at IEEE Aerospace Conference, Mar. 7-14, 2009, Big Sky, Montana, 6 pages.
International Search Report and Written Opinion for PCT/US2013/035935 dated Aug. 5, 2013, 9 pages.
International Preliminary Report on Patentability for PCT/US2013/035935, dated Oct. 23, 2014, 6 pages.
International Search Report and Written Opinion for International Patent Application No. PCT/US2015/026331, dated Jul. 6, 2015, 14 pages.
International Search Report and Written Opinion for International Patent Application No. PCT/US2015/026370, dated Jul. 6, 2015, 13 pages.
Notice of Allowance for U.S. Appl. No. 13/860,051, dated Apr. 11, 2017, 10 pages.
Examination Report for British Patent Application No. 1417673.9, dated Oct. 31, 2017, 6 pages.
Examination Report under Section 18(3) for United Kingdom Patent Application No. 1417673.9, dated Aug. 6, 2018, 5 pages.
Examination Report for Canadian Patent Application No. 2869923, dated Sep. 6, 2018, 3 pages.
Examination Report under Section 18(3) for United Kingdom Patent Application No. 1417673.9, dated Sep. 28, 2018, 3 pages.
Examination Report under Section 18(3) for United Kingdom Patent Application No. 1417673.9, dated Apr. 11, 2018, 8 pages.
Examination Report for Australian Patent Application No. 2015247413, dated Jun. 21, 2018, 3 pages.
Examination Report for Australian Patent Application No. 2015247437, dated Jun. 27, 2018, 4 pages.
Notice of Acceptance for Australian Patent Application No. 2015247437, dated Dec. 7, 2018, 3 pages.
Notice of Acceptance for Australian Patent Application No. 2015247413, dated Jan. 8, 2019, 3 pages.

* cited by examiner

PROGNOSTICS AND HEALTH MANAGEMENT SYSTEM

RELATED APPLICATIONS

This application claims the benefit of Provisional Patent Application Ser. No. 61/980,872, entitled "EFFICIENT METHOD FOR ENABLING PROGNOSTICS FOR BETTER HEALTH MANAGEMENT," filed Apr. 17, 2014, and Provisional Patent Application Ser. No. 62/067,050, entitled "EFFICIENT METHOD FOR ENABLING PROGNOSTICS FOR BETTER HEALTH MANAGEMENT," filed Oct. 22, 2014, the disclosures of each of which are hereby incorporated herein by reference in their entireties.

TECHNICAL FIELD

The embodiments relate generally to a prognostics and health management (PHM) system that utilizes one or more predictive learning models, separates the predictive learning models and other PHM analytics from a core PHM module, and facilitates the flexible extension of the PHM analytics without a need to alter the core PHM module.

BACKGROUND

Prognostics and health management (PHM) systems utilize a predictive learning model, such as a Neural Network, Bayesian Network, Support Vector Machine, or the like, to make predictions about a future state of an item, such as a component, sub-assembly, machine, or the like. The predicted future state may be when the item next needs maintenance, rebuilding, or replacement, for example. A PHM system may replace, or supplement, a time-based regime in which components undergo maintenance activities on a set schedule. Under such a regime, if a maintenance action is performed when it is not needed, ongoing operating costs are unnecessarily increased. By knowing which components are in need of maintenance and how soon such maintenance is required, maintenance actions can be planned in advance, while still limiting the amount of maintenance to only what is required based on the condition of the component. Among other advantages, a PHM system can provide improvement in asset availability and reduced maintenance costs and support an improved ability to plan for maintenance events.

A PHM system utilizes underlying PHM analytics and algorithms that intelligently process sensor data during operation of the machine. Generally, a PHM system includes processing raw sensor data that identifies real-time characteristics of components, training a predictive learning model based at least in part on the sensor data, and subsequently processing real-time sensor data with the predictive learning model to make predictions about future events, such as remaining useful life (RUL), time to maintenance, and the like.

Typically, the PHM system is a combination of hardware components and interrelated complex software components. Altering any aspects of the PHM analytics, such as altering the inputs to the predictive learning model, or the predictive learning model itself, requires modification of the PHM software, recompilation and debugging of the PHM software, downloading the PHM software to the machine, and re-booting the machine to implement the new PHM software. Modifying the PHM software requires a relatively skilled software technician who is knowledgeable in both the particular computer language in which the PHM software is written as well as the particular PHM software being modified, so that the modification does not result in unexpected problems. Such skilled technicians may be rare, resulting in desired modifications of the PHM analytics being delayed. Often, the user of the PHM system may have no capability of modifying the PHM system and, thus, must wait for the manufacturer of the PHM system to schedule the modification.

After the modification has been successfully implemented and tested, rolling out the modification to fleets of vehicles may be very time-consuming, and disruptive, such that each PHM system must be shut down, loaded with new PHM software, and then rebooted. This may be impractical in certain environments, such as a war zone.

SUMMARY

The embodiments include a prognostics and health management (PHM) system that separates PHM analytics from a PHM module that executes the PHM analytics, such that the PHM analytics can be relatively easily and quickly modified as desired and implemented by the PHM system without the need to load a new PHM module or, in some embodiments, without the need to even reboot the PHM module. The PHM analytics include predictive learning model parameter values that comprise values used by a corresponding predictive learning model to generate a predictive learning model output given one or more predictive learning model inputs. The PHM system also implements an extendable PHM architecture, wherein the PHM analytics can be developed using an English-based interpretable language, and can utilize custom-written externally invokable functions of the PHM module. Among other advantages, the embodiments allow relatively unskilled personnel to easily and intuitively modify the PHM analytics, and implement the modified PHM analytics without the need for a skilled software engineer, and without the need to modify a complex PHM module.

In one embodiment, a method for implementing prognostics health management (PHM) on a machine having a plurality of components is provided. Sensor data is generated that quantifies real-time conditions of components based on sensor signals generated by a plurality of corresponding sensors. A PHM system loads a PHM module generated at a first time and implements a plurality of externally invokable functions. The PHM system receives a first analytics script generated at a second time. The first analytics script comprises a plurality of first interpretable commands and a plurality of predictive learning model parameter values associated with a first predictive learning model. Some of the plurality of first interpretable commands are configured to invoke some of the plurality of externally invokable functions with at least some of the plurality of predictive learning model parameter values. The PHM module invokes a command interpreter module to interpret at least one first interpretable command and the at least some of the predictive learning model parameter values and generate first executable bytecodes. The first executable bytecodes execute to generate a notification identifying a predicted future condition of a first component for presentation on a display device based at least in part on at least some of the plurality of predictive learning model parameter values and the sensor data that quantifies the real-time condition of the first component.

In another embodiment, a PHM system for implementing PHM on a machine having a plurality of components is provided. The PHM system includes a sensor interface that is configured to be coupled to a plurality of sensors and a communication interface that is configured to communicate with a remote device. A controller comprising a processor is coupled to the sensor interface and the communication interface. The controller is configured to generate sensor data that quantifies the real-time conditions of the corresponding components based on sensor signals generated by a plurality of corresponding sensors. The controller is further configured to load a PHM module generated at a first time and implement a plurality of externally invokable functions. The PHM system is configured to receive a first analytics script generated at a second time. The first analytics script comprises a plurality of first interpretable commands and a plurality of predictive learning model parameter values associated with a first predictive learning model. Some of the plurality of first interpretable commands are configured to invoke some of the plurality of externally invokable functions with at least some of the plurality of predictive learning model parameter values. The controller is further configured to invoke, via the PHM module, a command interpreter module to interpret at least one first interpretable command and the at least some of the plurality of predictive learning model parameter values and generate first executable bytecodes. The controller is configured to execute the first executable bytecodes to generate a notification identifying a predicted future condition of a first component for presentation on a display device based at least in part on at least some of the plurality of predictive learning model parameter values and the sensor data that quantifies the real-time condition of the first component.

Those skilled in the art will appreciate the scope of the disclosure and realize additional aspects thereof after reading the following detailed description of the embodiments in association with the accompanying drawing figures.

BRIEF DESCRIPTION OF THE DRAWINGS

The accompanying drawing figures incorporated in and forming a part of this specification illustrate several aspects of the disclosure and, together with the description, serve to explain the principles of the disclosure.

DETAILED DESCRIPTION

The embodiments set forth below represent the information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

Any flowcharts discussed herein are necessarily discussed in some sequence for purposes of illustration, but unless otherwise explicitly indicated, the embodiments are not limited to any particular sequence of steps. The use herein of ordinals in conjunction with an element is solely for distinguishing what might otherwise be similar or identical labels, such as "first analytics script" and "second analytics script," and does not imply a priority, a type, an importance, or other attribute, unless otherwise stated herein.

The embodiments include a prognostics and health management (PHM) system that separates PHM analytics from a PHM module that executes the PHM analytics, such that the PHM analytics can be relatively easily and quickly modified as desired and implemented by the PHM system without the need to load a new PHM module or, in some embodiments, without the need to even reboot the PHM module. The PHM analytics include predictive learning model parameter values that comprise values used by a corresponding predictive learning model to generate a predictive learning model output given one or more predictive learning model inputs. The PHM system also implements an extendable PHM architecture, wherein the PHM analytics can be developed using an English-based interpretable language and can utilize custom-written externally invokable functions of the PHM module. Among other advantages, the embodiments allow relatively unskilled personnel to easily and intuitively modify the PHM analytics and implement the modified PHM analytics without the need for a skilled software engineer and without the need to modify a complex PHM module.

Figure 1:
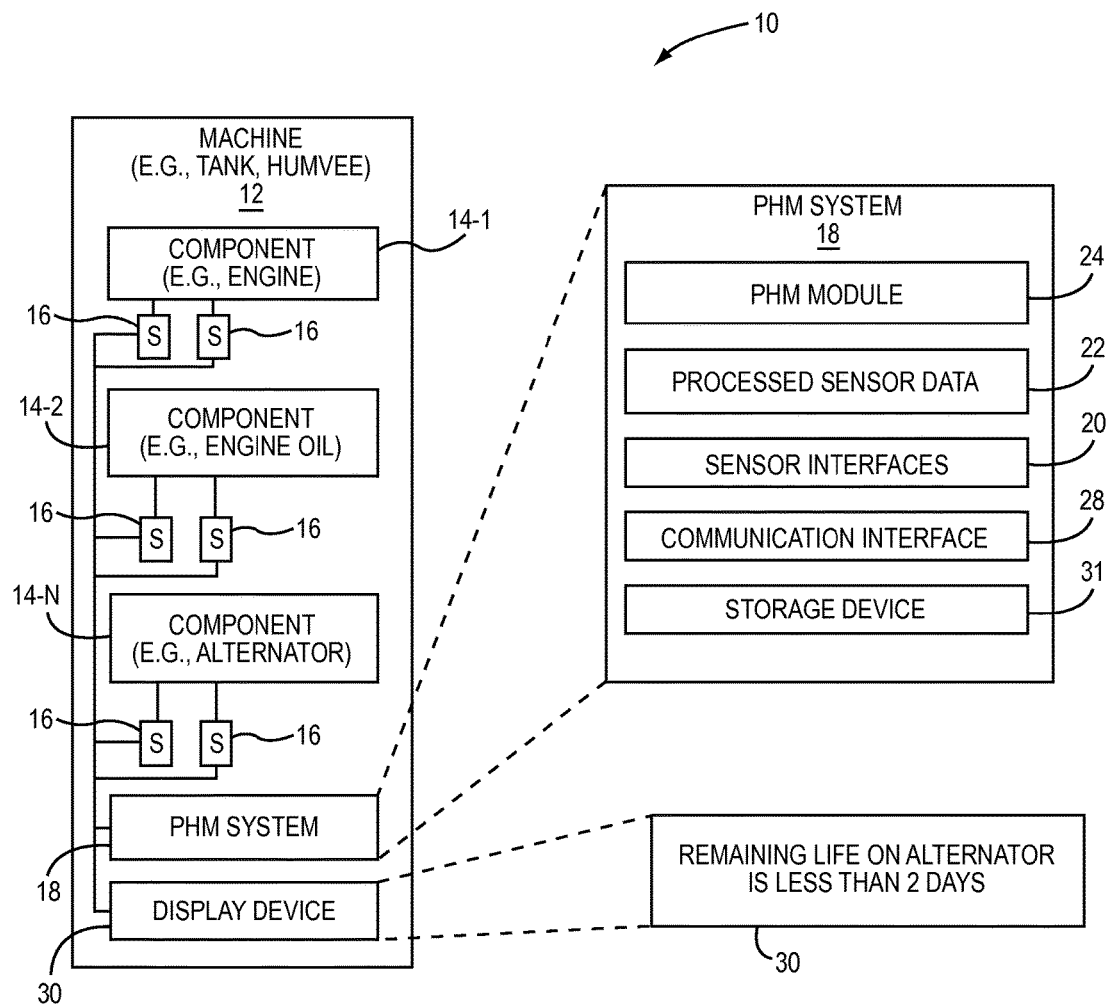
FIG. 1 is a block diagram of an environment in which embodiments may be practiced.

FIG. 1 is a block diagram of an environment 10 in which embodiments may be practiced. The environment 10 includes a machine 12 that includes a plurality of components 14-1-14-N (generally, components 14). The machine 12 can comprise any type of mobile or non-mobile device, such as, by way of non-limiting example, aircraft, such as airplanes and helicopters and the like; ground vehicles, such as cars, trucks, tanks, and the like; power turbines; windmills; or any other machine that includes a plurality of components whose characteristics may be sensed and quantified.

The components 14 may comprise any item whose characteristics may be sensed and quantified, such as, by way of non-limiting example, and in the context of a ground vehicle such as a Humvee, a transmission, an engine, a battery, hydraulic fluid, engine oil, transmission oil, a cabin, a fuel pump, an alternator, an air cleaner, and the like. The components 14 are continually or intermittently sensed by corresponding sensors 16. The sensors 16 may comprise any suitable sensor that is capable of sensing a desired real-time condition of the corresponding component 14 and generating a sensor signal that indicates a real-time condition of the component, such as vibrations, temperature, pressure, fluid level, voltage output, current output, moisture, and the like. A PHM system 18 includes one or more sensor interfaces 20 that are communicatively coupled to the sensors 16 and which receive the sensor signals generated by the sensors 16.

The PHM system 18, in one embodiment, comprises a printed circuit board that includes a plurality of integrated circuits and other electronics, and comprises one or more software modules, as discussed in greater detail herein, to provide certain PHM functionality. In other embodiments, the PHM system 18 comprises a computer, such as a laptop computer.

The PHM system 18 receives the sensor signals and processes the sensor signals to generate sensor data 22 that quantifies the real-time conditions of the components 14. Such processing may involve any desired or necessary computations or signal processing techniques, including filtering, analog-to-digital conversion, feature extraction such as the use of fast Fourier transforms to convert signals from a time domain to a frequency domain, and the like.

The PHM system 18 also includes a PHM module 24, which relatively continuously or periodically processes PHM analytics, as will be described in greater detail herein, based on and in response to the sensor data 22 or some other criteria, such as time. Such PHM analytics include instructions, or commands, for predicting future events, such as, by way of non-limiting example, the remaining useful life (RUL) of a component, a future time for maintenance of a component, a future time of failure of a component, and the like. As will be discussed in greater detail with reference to FIG. 2, the PHM analytics also include learning model parameter values associated with a predictive learning model, such as a Neural Network, Bayesian Network, Support Vector Machine, Regression Model, Gaussian Mixture Model, Hidden Markov Model, and the like.

The PHM module may, based on processing the PHM analytics, generate and present alerts on a display device 30 or other output device for presentation to an operator of the machine 12. In one embodiment, the PHM module 24 may be initiated, or otherwise loaded, from a PHM module instruction file (not illustrated) that comprises executable software instructions. The PHM module instruction file may be downloaded or otherwise installed on the PHM system 18, and the PHM system 18 may be booted, or restarted, to initiate the PHM module 24 from the PHM module instruction file. In some embodiments, the PHM module instruction file may be written in a complex computer programming language, such as C, Java, C++, or the like, and may comprise thousands or millions of lines of instructions. Thus, modifying the PHM module instruction file may be relatively complex, which would require a relatively highly skilled individual.

The PHM system 18 may also include one or more communication interfaces 28 that are configured to communicate with a remote device, such as a computer, via a network, and/or a flash drive device, such as a USB device. A storage device 31 may be used to store information, such as sensor data, the PHM module instruction file, or any other desired information.

Figure 2:
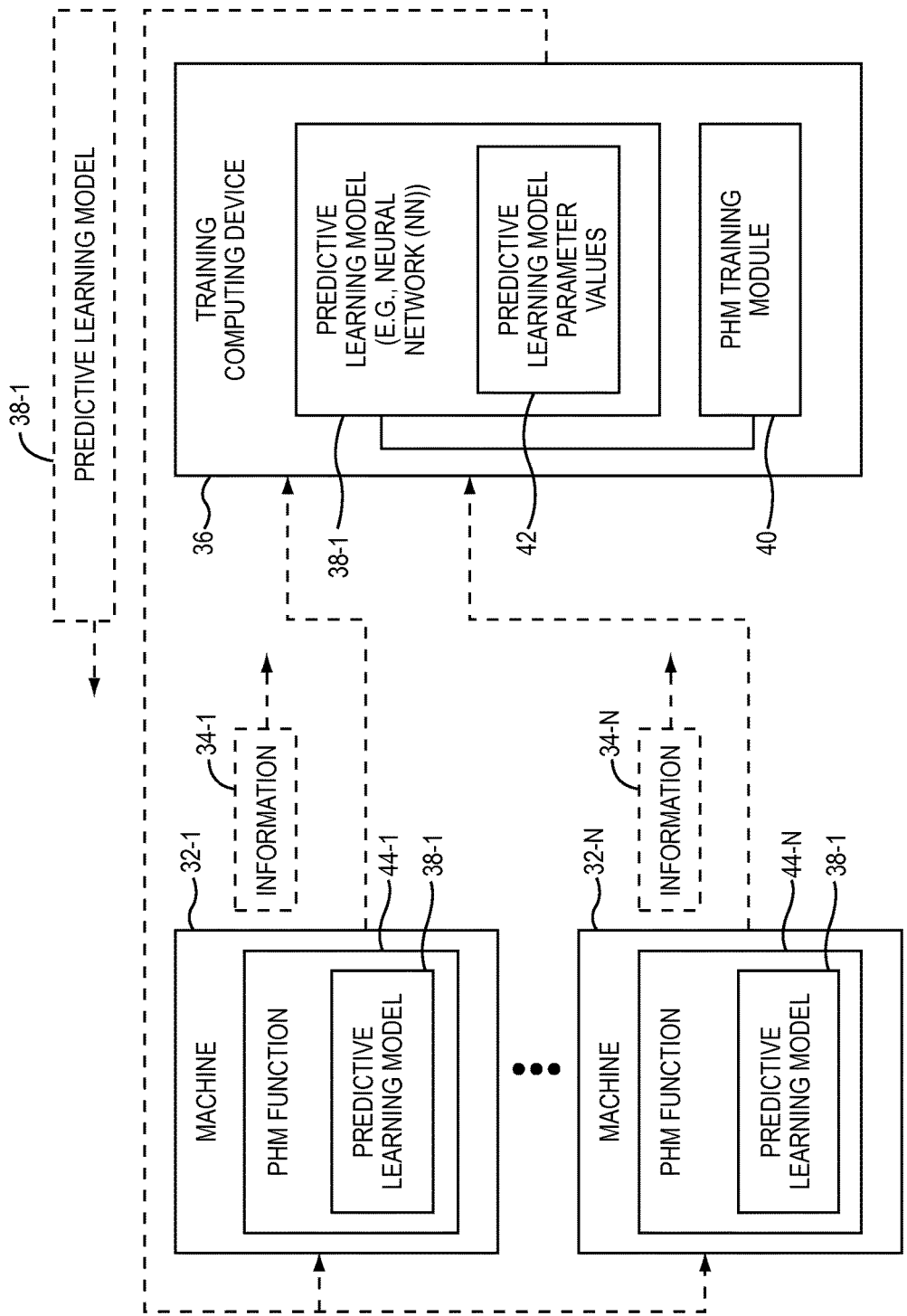
FIG. 2 is a block diagram illustrating a predictive learning model, according to one embodiment.

FIG. 2 is a block diagram illustrating a mechanism for utilizing a predictive learning model in a conventional manner. A plurality of machines 32-1-32-N (generally, machines 32) provide information 34-1-34-N (generally, information 34) to a training computing device 36. The information 34 comprises sensor data generated by sensors coupled to components of the machines 32. The information 34 may also include event information that identifies events that have occurred with respect to the machines 32, including component failure, component end of life, and the like. The machines 32 can comprise any desired type of machine, such as ground vehicles, airborne vehicles, or plant equipment. While, for purposes of illustration, only two machines 32 are illustrated, information 34 from hundreds or thousands of machines 32 may be collected over time and provided to the training computing device 36.

The training computing device 36 includes a predictive learning model 38-1, such as, by way of non-limiting example, a Neural Network, Bayesian Network, Support Vector Machine, Regression Model, Gaussian Mixture Model, Hidden Markov Model, or the like. A PHM training module 40 trains the predictive learning model 38-1 using the information 34. The training process results in the calculation of predictive learning model parameter values 42. The predictive learning model parameter values 42 comprise the parameters used by the predictive learning model 38-1 to determine an output of the predictive learning model 38-1 given one or more inputs. In the context of a neural network, the predictive learning model parameter values 42 comprise weights. In types of predictive learning models 38 other than a neural network, the predictive learning model parameter values 42 may comprise other data. The goal is for the predictive learning model 38-1 to derive predictive learning model parameter values 42 that provide the most accurate outputs (i.e., most likely to be correct) in view of the one or more inputs. Typically, as the predictive learning model 38-1 is trained over time by the information 34, the predictive learning model parameter values 42 change in a manner that provides better and more accurate outputs.

After the predictive learning model 38-1 is trained, the predictive learning model 38-1 may be installed on the machines 32 as part of respective PHM functions 44-1-44-N for use in making predictions regarding future conditions of the respective machines 32 or components of the respective machines 32. In order to utilize the predictive learning model 38-1, the PHM functions 44-1-44-N must be modified and recompiled by skilled software engineers. The current versions of the PHM functions 44-1-44-N must then be terminated on the machines 32, and the new PHM functions 44-1-44-N must be installed on the machines 32. This process is complex, time-consuming, requires highly skilled labor, and disrupts service on the machines 32.

After installation and subsequent operation of the machines 32, additional information 34 is generated and provided to the training computing device 36 over time, and the predictive learning model 38-1 is further trained and updated based on such additional information 34, resulting in the generation of different, and likely more accurate, predictive learning model parameter values 42. In order to provide the updated predictive learning model 38-1 to the machines 32, the same disruptive installation process must be repeated.

Figure 3:
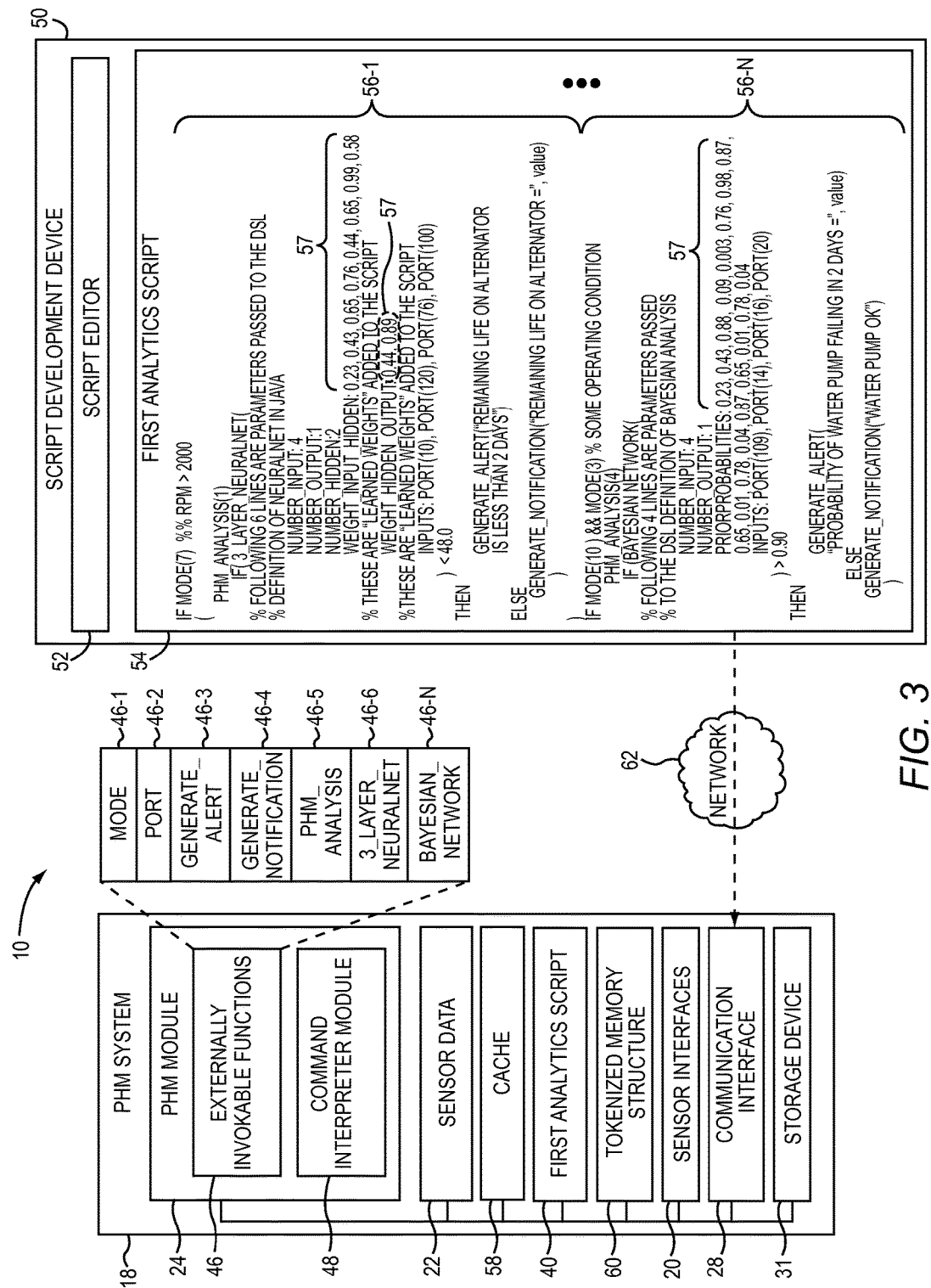
FIG. 3 is a block diagram of the environment illustrated in FIG. 1 illustrating a PHM system in greater detail, according to one embodiment.

FIG. 3 is a block diagram of the environment 10 illustrating the PHM system 18 in greater detail according to one embodiment. Solely due to space constraints, the machine 12 is not illustrated. In some embodiments, the PHM module 24 includes one or more externally invokable functions 46-1-46-N (generally, externally invokable functions 46). In one embodiment, the PHM module 24 is written in a first computer programming language, such as C, C++, Java, or the like, which allows the generation of functions which may be invoked by external independent programs. While only seven externally invokable functions 46 are illustrated, the embodiments are not so limited, and the PHM module 24 can be written with any number of externally invokable functions 46. The externally invokable functions 46 are integral to the PHM module 24 and, as such, can access and otherwise manipulate any data that is capable of being accessed and manipulated by the PHM module 24. The externally invokable functions 46 therefore provide a mechanism by which external and independent processes can be developed and, at run-time, can implement certain behavior of the PHM module 24. As will be discussed herein in greater detail, each externally invokable function 46 may be utilized in analytic commands for implementing PHM analytics in the PHM system 18. The externally invokable functions 46 can thus be utilized to extend an existing language, such as a scripting language, to generate a domain specific language that is unique to and centered on generating PHM analytics for use with the PHM system 18.

The PHM module 24 includes a command interpreter module 48 that is configured to interpret commands written in a second interpretable programming language at run-time. The command interpreter module 48 can comprise any interpreter for any suitable interpretable programming language. In one embodiment, the command interpreter module 48 comprises a Lua interpreter, available from LabLua, a laboratory of the Department of Computer Science of PUC-Rio, and the interpretable programming language comprises Lua. The command interpreter module 48 is configured to receive an interpretable command and generate executable bytecodes based on the interpretable command. The executable bytecodes may then be executed to implement the interpretable command. The command interpreter module 48 can also be developed to interpret interpretable commands that utilize one or more of the externally invokable functions 46, and to generate executable bytecodes that invoke the externally invokable functions 46 with one or more predictive learning model parameter values 42.

In one embodiment, a script development device 50 may include a script editor 52 to facilitate the generation of a first analytics script 54. The script development device 50 can comprise any suitable data processing device, such as, by way of non-limiting example, a desktop or laptop computer, a computing tablet, a smart phone, or the like. The script editor 52 may comprise any suitable editor and, in one embodiment, may be provided in conjunction with a particular interpretable language, such as, by way of non-limiting example, the Lua scripting language. The first analytics script 54 contains a plurality of interpretable commands 56-1-56-N (generally, interpretable commands 56) that are interpretable by the command interpreter module 48 and which implement the PHM analytics for the PHM system 18. Generally, the PHM analytics evaluate real-time conditions of the machine 12 via the sensor data 22 based on one or more predictive learning model parameter values 57 to predict a future condition of a component 14 of the machine 12. The prediction can be expressed as a notification for presentation to an operator. Such notifications may be merely informative, such as notifying the operator that an RUL of the component 14 is months away, or can be in the form of an alert, such as notifying the operator that there is a predicted imminent failure of the component 14.

Similar to the manner discussed above with regard to FIG. 2, the predictive learning model parameter values 57 are derived by an associated predictive learning model, such as a neural network, Bayesian Network, and the like, and comprise values, such as weights, used by the associated predictive learning model to generate an output in response to one or more inputs to the associated predictive learning model. However, in contrast to the PHM system 18 discussed in FIG. 2, the embodiments provide the predictive learning model parameter values 57 in the first analytics script 54, eliminating the need to recompile, debug, and reinstall the PHM module 24 each time the associated predictive learning model is trained. Among other advantages, this allows the PHM module 24 to be continually updated with the most recent, and accurate, predictive learning model parameter values 57 after training the associated predictive learning model without disruption to the PHM module 24 or the PHM system 18.

The interpretable commands 56 include English language words, such as "MODE," "PORT," "IF," and the like, and are thus easily understood by individuals who are familiar with the English language, even individuals that are not relatively skilled software developers. The interpretable commands 56 may thus be generated and subsequently revised or updated by more readily available personnel than skilled software developers. This ability makes it relatively easy to change the PHM analytics of the PHM system 18 as desired.

Note also that certain of the English language words utilized in the interpretable commands 56 are the names of the externally invokable functions 46, such as "3_LAYER_NEURALNET" and "BAYESIAN_NETWORK." The use of such words will cause, during processing of the first analytics script 54, the invocation of and execution of the corresponding externally invokable function 46. Thus, the embodiments allow the intuitive generation of customized functionality in the PHM system 18 in the form of the externally invokable functions 46, which may be accessed and leveraged using an easily understood, English-language- (or other natural language) based command structure. In essence, the embodiments allow an existing interpretable programming language, such as, in this example, the Lua scripting language, to be extended to include commands unique to the PHM system 18.

In this example, the externally invokable functions 46 provide the following functionality, but the embodiments are not limited to any particular externally invokable functions 46. The PHM module 24 may be designed to implement any number of externally invokable functions 46 implementing any desired functionality. The externally invokable function 46-1 ("MODE") returns a Boolean state of a component, subsystem, or other entity. The determination of a mode may include analyzing the sensor data 22 to determine a True or False value. The externally invokable function 46-2 ("PORT") allows access to a particular source of sensor data 22. For example, PORT(190) may allow access to sensor data 22 that indicates revolutions per minute of an engine, and PORT(100) may allow access to sensor data 22 that indicates an oil pressure. The externally invokable function 46-3 ("GENERATE_ALERT") causes the presentation of a notification in the form of an alert on the display device 30. The externally invokable function 46-4 ("GENERATE_NOTIFICATION") causes the presentation of a notification on the display device 30. The externally invokable function 46-5 (PHM_ANALYSIS) invokes the high-level processing associated with any type of predictive learning model. The externally invokable function 46-6 ("3_LAYER_NEURALNET") invokes the specific processing associated with a neural network predictive learning model. The externally invokable function 46-6 may accept the predictive learning model parameter values 57 provided in the first analytics script 54 and perform the processing associated with the associated predictive learning model, in this example, a 3-layer neural network, and thus implements the functionality associated with the predictive learning model without having to continually install a new predictive learning model on the PHM system 18. The externally invokable function 46-N ("BAYESIAN_NETWORK") similarly invokes the processing associated with a Bayesian Network predictive learning model and may accept as parameters corresponding predictive learning model parameter values 57 provided in the first analytics script 54. Thus, the PHM system 18 may implement multiple different predictive learning models for predicting future conditions of components 14. Any number of predictive learning models may be encoded into the PHM module 24 and utilized by including corresponding predictive learning model parameter values 57 in the appropriate interpretable commands 56 of the first analytics script 54.

While not illustrated in FIG. 3, additional example externally invokable functions may include an INTERVAL externally invokable function that defines how frequently the analytics should be processed. SUM, AVERAGE, MEAN and other mathematical externally invokable functions may be generated to support any math functions needed by the PHM analytics. A CONDITION externally invokable function defines logical relations among variables. Such conditions may be used to store the validity of a condition or expression that may be used by the system in an evaluation in order to generate a notification.

After development of the first analytics script 54, the first analytics script 54 may be provided to the PHM system 18. The first analytics script 54 may be provided in any desired manner, such as via a wired or wireless network 62. Alternatively, the first analytics script 54 may be stored in a portable storage device such as a USB flash drive, which in turn may be coupled to a USB port of the PHM system 18. The PHM system 18 may then download the first analytics script 54 from the USB flash drive and store the first analytics script 54 in the storage device 31 for subsequent use by the PHM system 18 for implementing analytics in the PHM system 18. Note that the interpretable commands 56 contained in the first analytics script 54 are in the form of English language words and are thus not directly executable by the PHM system 18. Rather, the interpretable commands 56 are only executable after being translated into an executable bytecode form by the command interpreter module 48.

The PHM system 18 may also include a cache 58, which may be used, for example, to store short-term historical data associated with the PHM system 18, such as, by way of non-limiting example, sensor data 22 and modes associated with components 14. Among other things, the data stored in the cache 58 may be utilized to determine rates of changes of the sensor data 22.

As will be described in greater detail herein, in one embodiment, the PHM system 18 may directly, or via a token parser module (not illustrated), initially process the first analytics script 54 and generate a tokenized memory structure 60. The tokenized memory structure 60 may provide an efficient and condensed mechanism for access to the interpretable commands 56 during PHM processing by the PHM module 24.

Figure 4A:
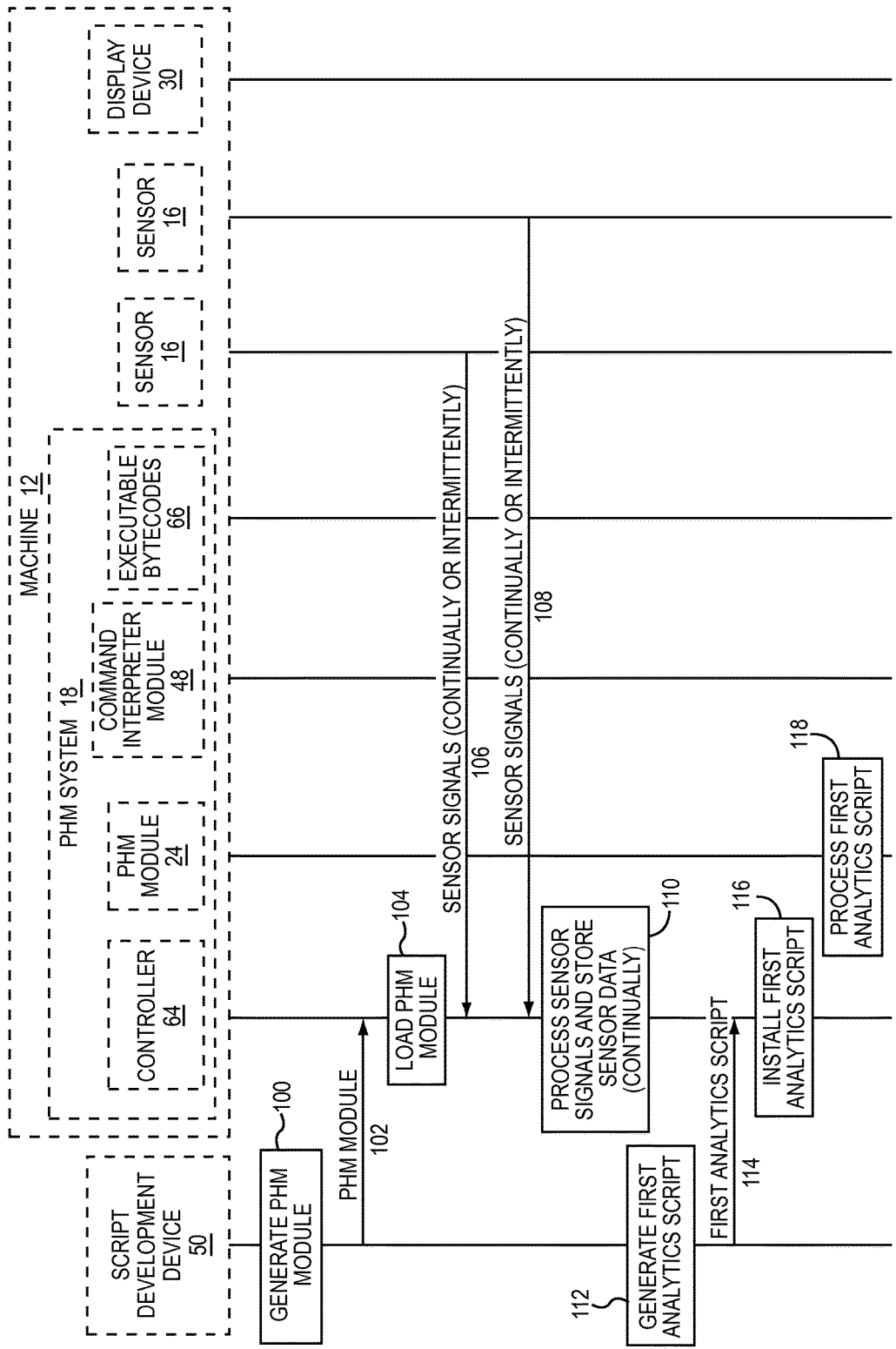
FIGS. 4A-4B are message flow diagrams illustrating an example message flow of the PHM system, according to one embodiment.
Figure 4B:
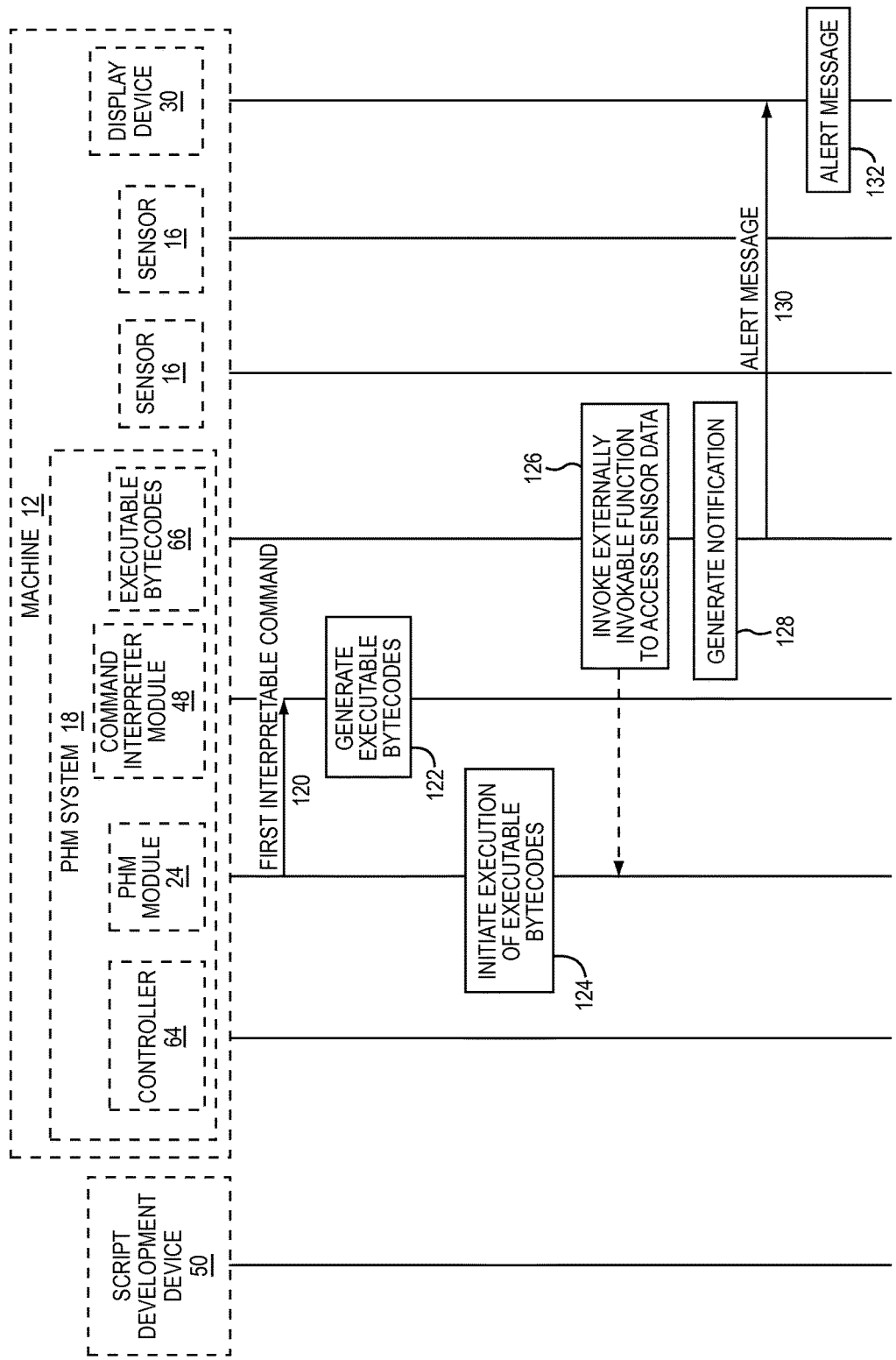

FIGS. 4A-4B are message flow diagrams illustrating an example message flow of the PHM system 18 according to one embodiment. Initially, an engineer designs and generates the PHM module 24 on the script development device 50 (block 100). As discussed above, the PHM module 24 may be developed in a first programming language having a first syntax, such as C, C++, Java, or the like. The engineer includes in the PHM module 24 any desired externally invokable functions 46. The engineer compiles first programming language instructions to generate an executable file and provides the executable file to the PHM system 18 (block 102). The PHM system 18 (via a controller 64 in this example) loads the PHM module 24 (block 104). This may include, for example, rebooting the PHM system 18 to remove a prior version of the PHM module 24 from a memory of the PHM system 18 and installing a new version of the PHM module 24. This may disrupt the operation of the PHM system 18 for a period of time.

The controller 64 may continually, or intermittently, receive sensor signals from the corresponding sensors 16 of the PHM system 18 (blocks 106-108). This may occur independently of and parallel to processing performed by the PHM module 24. The controller 64 continually processes the sensor signals, as discussed above, to generate the sensor data 22 (block 110). At some point in time, an operator or other individual generates the first analytics script 54 on the script development device 50 (sometimes referred to herein as a remote device) (block 112). The first analytics script 54 is written in a second programming language having a second syntax that is different from the first programming language. The second programming language is preferably an English-word-based programming language that is easily understood by individuals that may not be skilled software developers. The first analytics script 54 comprises a plurality of interpretable commands 56 that implement the desired PHM analytics of the PHM system 18.

The first analytics script 54 is provided to the PHM system 18 (block 114). For example, the PHM system 18 may be temporarily or permanently communicatively coupled to the script development device 50 via the network 62. Alternatively, the first analytics script 54 may be provided to the PHM system 18 via a portable storage device, such as a USB flash drive device, for example. The PHM system 18 stores, or otherwise installs, the first analytics script 54 on the PHM system 18 (block 116). The PHM module 24 may then begin to process the first analytics script 54 (block 118). In some embodiments, in order to process the first analytics script 54, the PHM module 24 may first be terminated, and then reloaded. In other embodiments, the PHM module 24 may be designed such that a command may be utilized to instruct the PHM module 24 to discard a previous analytics script and load a new analytics script.

The initial processing may involve tokenizing the first analytics script 54 to generate the tokenized memory structure 60. In addition to interpretable commands 56 that include predictive learning model parameter values 57, the first analytics script 54 may include configuration statements or commands for use by the PHM module 24. In one embodiment, during an initial phase of processing, the PHM module 24 assigns, based on the first analytics script 54, each corresponding sensor 16 a corresponding port value. The interpretable commands 56 are configured to access the sensor data 22 associated with a corresponding sensor 16 based on the corresponding port value.

Generally, the PHM module 24 operates in a continuous manner, and implements interpretable commands 56 in response to an event, such as the receipt of a sensor signal from a sensor 16 or the expiration of a timer. For example, the PHM module 24 may process particular interpretable commands 56 periodically, as defined in the first analytics script 54 utilizing, for example, the INTERVAL command discussed above. Upon such an event, the PHM module 24 accesses one or more interpretable commands 56 that are to be processed upon the occurrence of such an event. The correlation between events and the one or more interpretable commands 56 may be defined in the first analytics script 54.

For purposes of illustration, assume that such an event occurs. The PHM module 24 accesses the tokenized memory structure 60 and identifies a first interpretable command 56 associated with the event. The PHM module 24 passes the first interpretable command 56 to the command interpreter module 48 (block 120). The command interpreter module 48 interprets the first interpretable command 56 and the predictive learning model parameter values 57 and generates executable bytecodes 66 that are suitable for execution on the machine 12 (block 122). In one embodiment, the executable bytecodes 66 may comprise Java bytecodes that can be executed by a Java Virtual Machine. In other embodiments, the executable bytecodes 66 may comprise native bytecodes directly executable by the particular processing device of the PHM system 18. The command interpreter module 48 generates executable bytecodes 66 that are configured to invoke the one or more externally invokable functions 46 with the appropriate predictive learning model parameter values 57 that are identified in the first interpretable command 56.

The PHM module 24 then initiates execution of the executable bytecodes 66 (block 124). The executable bytecodes 66 execute to implement the functionality of the corresponding interpretable command 56. For example, the executable bytecodes 66 may invoke an externally invokable function 46 with the predictive learning model parameter values 57 to access the sensor data 22 and may generate a notification that contains a prediction of a future condition of the component 14 from which the sensor data 22 originated (block 128). For example, the executable bytecodes 66, based on the sensor data 22 and the predictive learning model parameter values 57, may determine that the component 14 is predicted to fail within two (2) days. The executable bytecodes 66 may communicate the notification in the form of an alert message to the display device 30 that indicates that the component 14 is predicted to fail within two (2) days (block 130). The display device 30 may present the alert message to the operator of the PHM system 18 (block 132).

Figure 5:
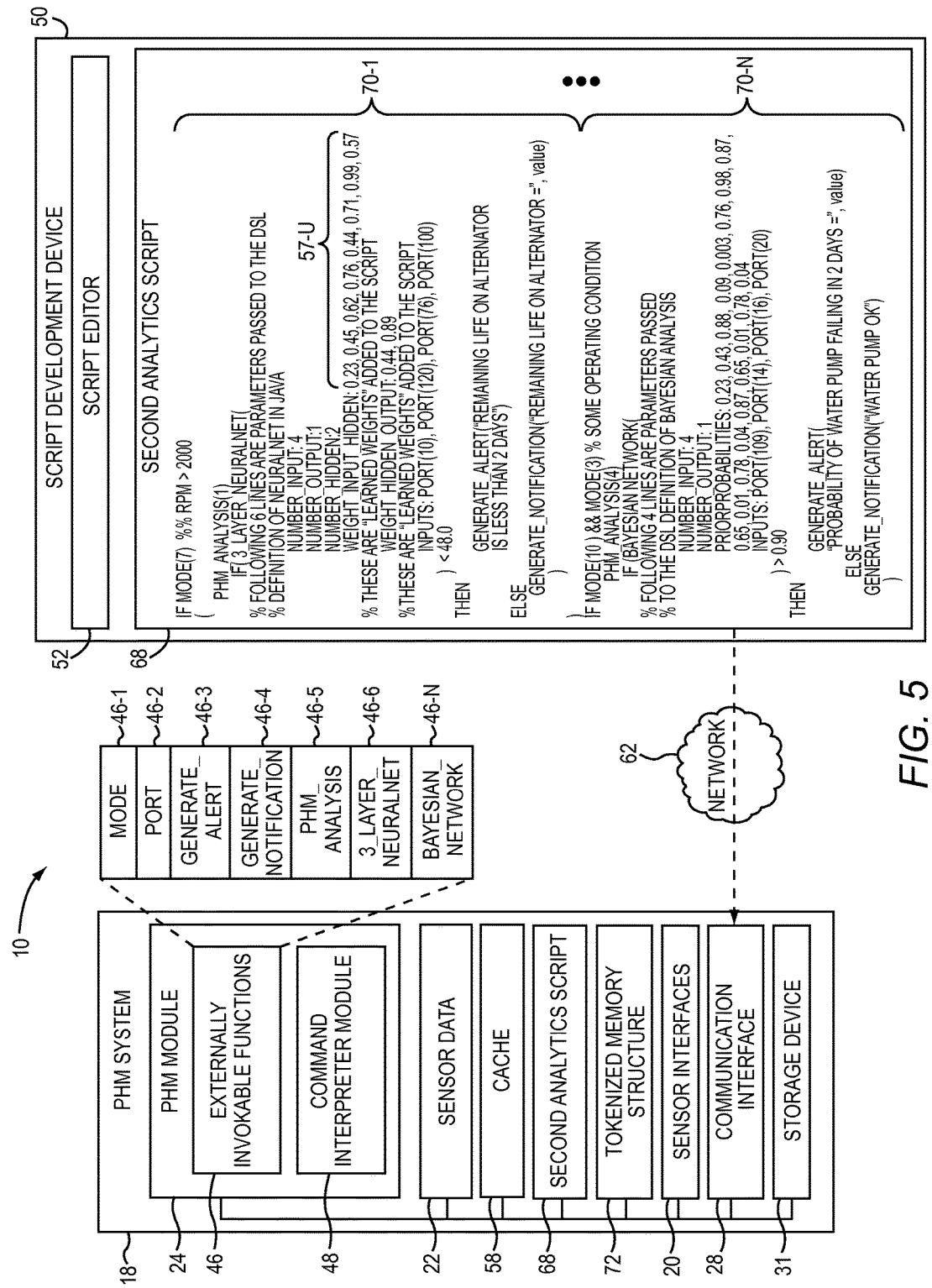
FIG. 5 is a block diagram of the environment at a point in time subsequent to that illustrated in FIG. 3, according to one embodiment.

FIG. 5 is a block diagram of the environment 10 at a point in time subsequent to that illustrated in FIG. 3 according to one embodiment. In this embodiment, assume that the first analytics script 54 included a first interpretable command 56-1 that predicted the RUL of the component 14-N based on the sensor data 22 and in conjunction with certain predictive learning model parameter values 57 contained in the first interpretable command 56-1 (an alternator, in this example).

Further assume that the associated predictive learning model has been subsequently trained with additional information, and has derived different, more accurate predictive learning model parameter values 57 for determining the RUL of the component 14-N. An operator may then modify, on the script development device 50, via the script editor 52, the first analytics script 54 to generate a second analytics script 68 that comprises one or more second interpretable commands 70-1-70-N, including a second interpretable command 70-1 that contains updated predictive learning model parameter values 57-U derived by the associated predictive learning model after the additional training. The second analytics script 68 can then be provided to the PHM system 18 to replace the first analytics script 54. The PHM system 18 processes and parses the second analytics script 68 to generate a tokenized memory structure 72, and thereafter the prediction associated with the RUL of the component 14-N will be based on the updated predictive learning model parameter values 57-U rather than the predictive learning model parameter values 57 contained in the first analytics script 54. Note that the PHM analytics implemented via the second analytics script 68 were changed without any change to the PHM module 24. Thus, it was not necessary to modify the PHM module 24, recompile the PHM module 24, and install the PHM module 24 on the PHM system 18 to alter the PHM analytics implemented by the PHM module 24.

Figure 6:
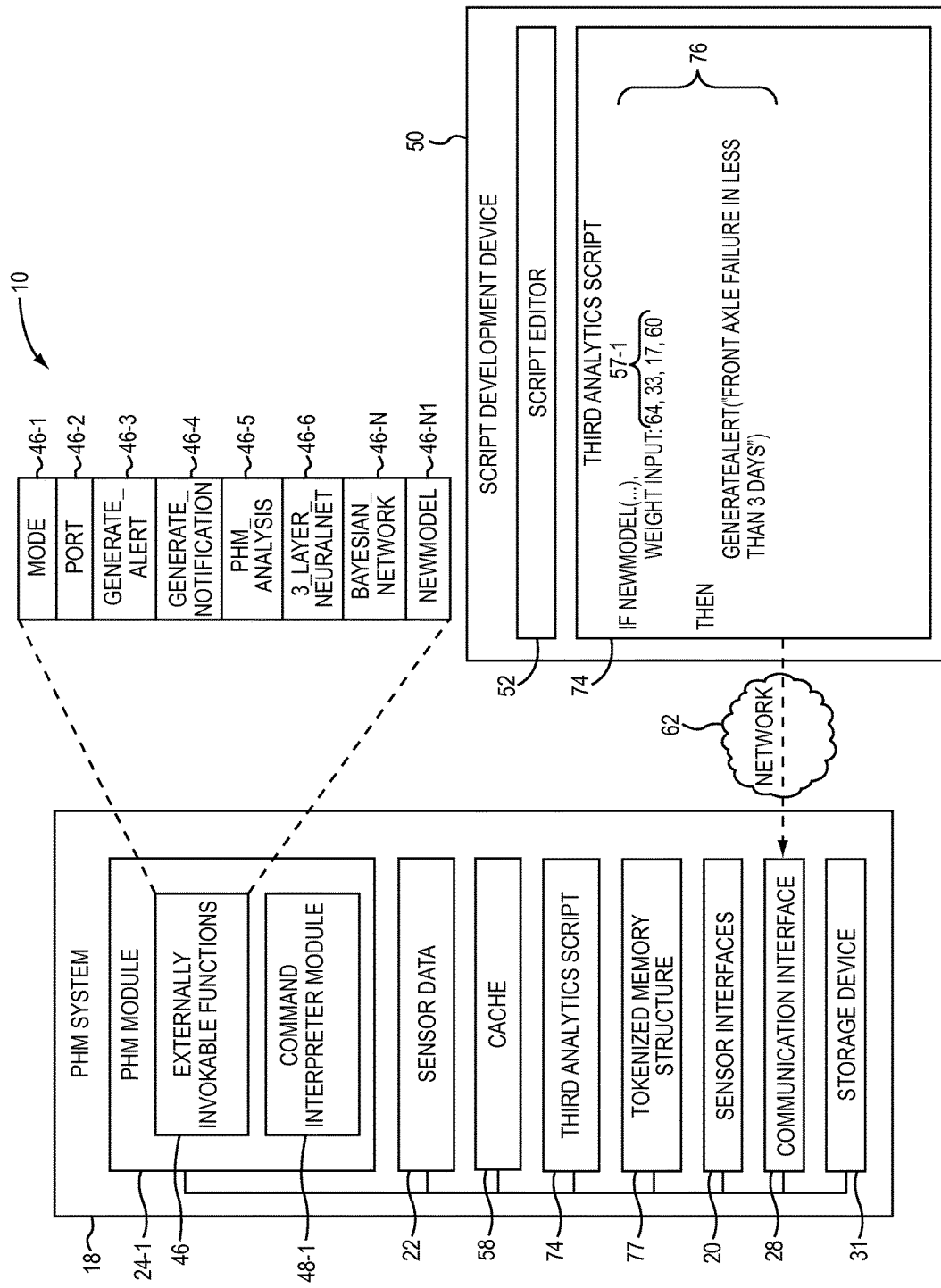
FIG. 6 is a block diagram of the environment at a point in time subsequent to that illustrated in FIG. 5, according to one embodiment.

FIG. 6 is a block diagram of the environment 10 at a point in time subsequent to that illustrated in FIG. 4 according to one embodiment. In this embodiment, assume that the manufacturer of the PHM module 24 desires to implement, or extend, the second programming language used to generate interpretable commands to implement processing associated with an additional predictive learning model. The manufacturer implements this new functionality in a command entitled "NEWMODEL," which allows interpretable commands to implement predictions from the additional predictive learning model. The manufacturer generates a new externally invokable function 46-N1 in a new PHM module 24-1. A new command interpreter module 48-1 is generated in order to enable the command interpreter module 48-1 to interpret the new interpretable command and in order generate suitable executable bytecodes for invoking the externally invokable function 46-N1. The PHM module 24-1 is then installed on the PHM system 18 to replace the PHM module 24. An individual may then develop a third analytics script 74 that includes a third interpretable command 76 that utilizes the new command "NEWMODEL" and contains predictive learning model parameter values 57-1 associated with the new predictive learning model. The third analytics script 74 may be provided to the PHM system 18 to replace a previous analytics script, such as the second analytics script 68. The PHM module 24-1 may initially parse, or have parsed, the third analytics script 74 to generate a new tokenized memory structure 77. Upon the occurrence of the corresponding event, the PHM module 24-1 may access the third interpretable command 76 and pass the third interpretable command 76 and the predictive learning model parameter values 57-1 to the command interpreter module 48-1 for interpretation and the generation of suitable executable bytecodes 66. The command interpreter module 48-1 generates executable bytecodes 66, which, when executed, invoke the externally invokable function 46-N1 with the predictive learning model parameter values 57-1.

Figure 7:
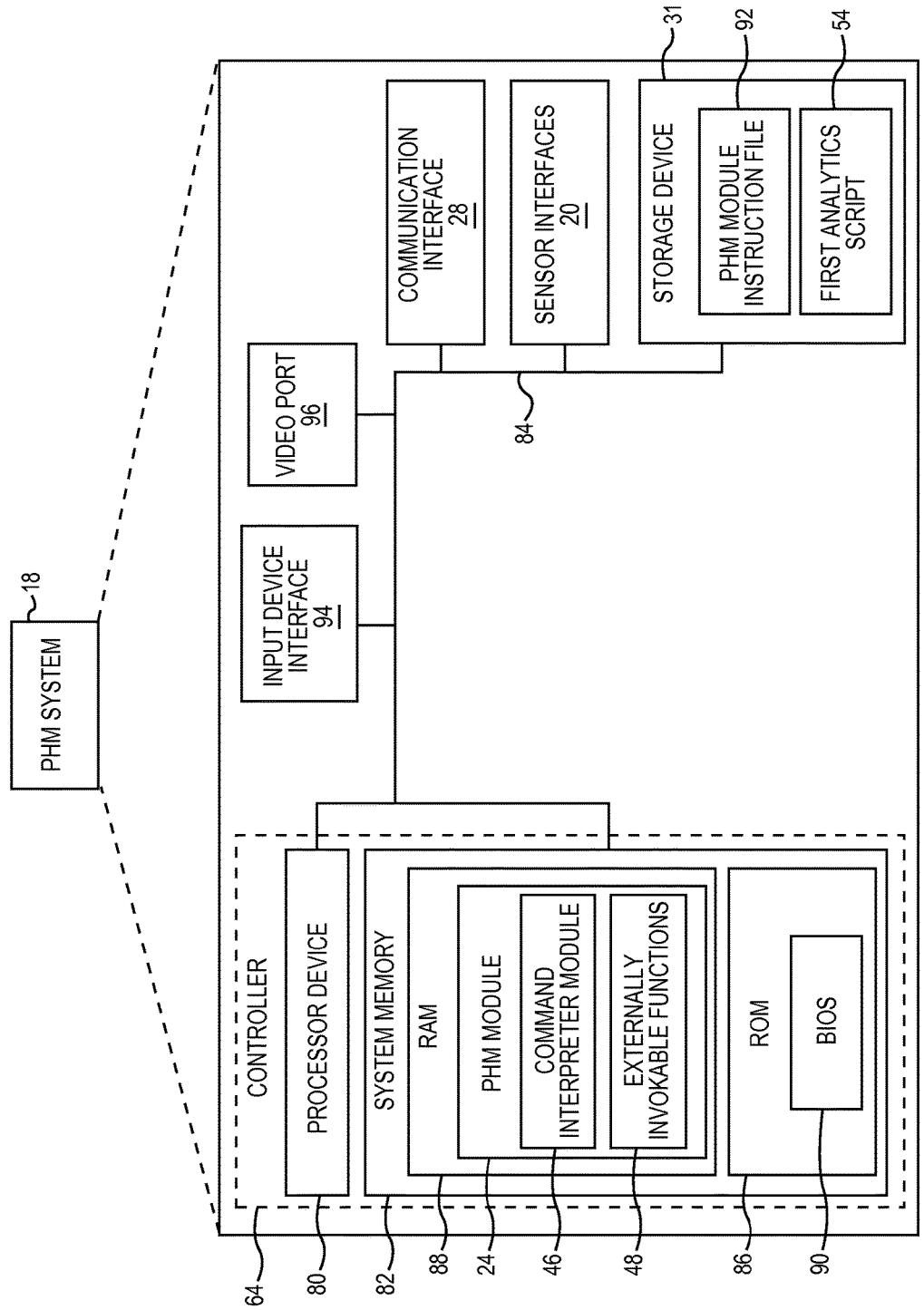
FIG. 7 is a block diagram of the PHM system, according to one embodiment.

FIG. 7 is a block diagram of the PHM system 18 according to one embodiment. The PHM system 18 may comprise any computing or processing device capable of including firmware or hardware and/or executing software instructions to implement the functionality described herein, such as a printed circuit board, laptop or desktop computer, computing table, or the like. The PHM system 18 includes a processor device 80, a system memory 82, and a system bus 84. The system bus 84 provides an interface for system components including, but not limited to, the system memory 82 and the processor device 80. The processor device 80 can be any commercially available or proprietary processor.

The system bus 84 may be any of several types of bus structures that may further interconnect to a memory bus (with or without a memory controller), a peripheral bus, and/or a local bus using any of a variety of commercially available bus architectures. The system memory 82 may include non-volatile memory 86 (e.g., read-only memory (ROM), erasable programmable read-only memory (EPROM), electrically erasable programmable read-only memory (EEPROM, etc.), and/or volatile memory 88 (e.g., random access memory (RAM)). A basic input/output system (BIOS) 90 may be stored in the non-volatile memory 86, and can include the basic routines that help transfer information between elements within the PHM system 18. The volatile memory 88 may also include a high-speed RAM, such as static RAM for caching data.

The PHM system 18 may further include or be coupled to the storage device 31, which may comprise, for example, an internal or external hard disk drive (HDD) (e.g., enhanced integrated drive electronics (EIDE) or serial advanced technology attachment (SATA)), HDD (e.g., EIDE or SATA) for storage, flash memory, or the like. The storage device 31 and other drives associated with computer-readable media and computer-usable media may provide non-volatile storage of data, data structures, computer-executable instructions, and the like. Although the description of computer-readable media above refers to an HDD, it should be appreciated by those skilled in the art that other types of media which are readable by a computer, such as Zip disks, magnetic cassettes, flash memory cards, cartridges, and the like, may also be used in the exemplary operating environment and, further, that any such media may contain computer-executable instructions for performing novel methods of the disclosed architecture. The storage device 31 may store a PHM module instruction file 92 that, in one embodiment, contains the executable instructions that implement the PHM module 24. The storage device 31 may also store the first analytics script 54.

A number of modules can be loaded into the volatile memory 88, including the PHM module 24, the command interpreter module 48, and the externally invokable functions 46. An operating system (not illustrated) and the PHM module 24, the command interpreter module 48, and the externally invokable functions 46 may implement the functionality described herein in whole or in part. It is to be appreciated that the embodiments can be implemented with various commercially available operating systems or proprietary operating systems.

All or a portion of the embodiments may be implemented as a computer program product stored on a transitory or non-transitory computer-usable or computer-readable storage medium, such as the storage device 31, which includes complex programming instructions, such as complex computer-readable program code, configured to cause the processor device 80 to carry out the steps described herein. Thus, the computer-readable program code can comprise software instructions for implementing the functionality of the embodiments described herein when executed on the processor device 80. The processor device 80, in conjunction with the PHM module 24, the command interpreter module 48, and the externally invokable functions 46 in the volatile memory 88, may serve as the controller 64 for the PHM system 18 that is configured to, or adapted to, implement the functionality described herein.

An operator may also be able to enter commands to the PHM system 18 through a keyboard (not illustrated), a pointing device such as a mouse (not illustrated), or a touch-sensitive surface (not illustrated). Such input devices may be connected to the processor device 80 through an input device interface 94 that is coupled to the system bus 84 but can be connected by other interfaces such as a parallel port, an Institute of Electrical and Electronic Engineers (IEEE) 1394 serial port, a Universal Serial Bus (USB) port, an IR interface, and the like.

The PHM system 18 may also include the communication interface 28, suitable for communicating with the network 62 and other networks as appropriate or desired. The PHM system 18 may also include a video port 96 configured to interface with the display device 30 to provide the operator with notifications as appropriate.

Those skilled in the art will recognize improvements and modifications to the preferred embodiments of the disclosure. All such improvements and modifications are considered within the scope of the concepts disclosed herein and the claims that follow.

What is claimed is:

1. A method for implementing prognostics health management (PHM) on a machine having a plurality of components, comprising:
    generating sensor data that quantifies real-time conditions of the plurality of components based on sensor signals generated by a plurality of corresponding sensors;
    loading, by a PHM system, a PHM module generated at a first time and implementing a plurality of externally invokable functions;
    receiving, by the PHM system, a first analytics script generated at a second time, the first analytics script comprising a plurality of first interpretable commands and a plurality of predictive learning model parameter values associated with a first predictive learning model, some of the plurality of first interpretable commands configured to invoke some of the plurality of externally invokable functions with at least some of the plurality of predictive learning model parameter values;
    invoking, by the PHM module, a command interpreter module to interpret at least one first interpretable command and the at least some of the plurality of predictive learning model parameter values and generate first executable bytecodes based on the at least one first interpretable command and the at least some of the plurality of predictive learning model parameter values, the first executable bytecodes configured to invoke the at least some of the plurality of externally invokable functions with the at least some of the plurality of predictive learning model parameter values identified in the at least one first interpretable command; and
    executing the first executable bytecodes to generate a notification identifying a predicted future condition of a first component for presentation on a display device based at least in part on the at least some of the plurality of predictive learning model parameter values and the sensor data that quantifies the real-time condition of the first component.

2. The method of claim 1, wherein generating the sensor data that quantifies the real-time conditions of the plurality of components based on the sensor signals generated by the plurality of corresponding sensors comprises:
    receiving, by the PHM system, the sensor signals generated by the plurality of corresponding sensors, the sensor signals indicating the real-time conditions of the plurality of components; and
    processing the sensor signals to generate the sensor data that quantifies the real-time conditions of the plurality of components.

3. The method of claim 1, wherein processing the sensor signals to generate the sensor data that quantifies the real-time conditions of the plurality of components comprises filtering the sensor signals and extracting features from the sensor signals to generate the sensor data.

4. The method of claim 1, wherein the first predictive learning model comprises a neural network and the plurality of predictive learning model parameter values comprises neural network weights generated by the neural network during a training phase of the neural network.

5. The method of claim 1, further comprising:
    detecting, by the PHM module, the at least one first interpretable command in the first analytics script, the at least one first interpretable command configured to invoke a first externally invokable function of the plurality of externally invokable functions with the at least some of the plurality of predictive learning model parameter values; and wherein invoking the command interpreter module to interpret the at least one first interpretable command and generate the first executable bytecodes further comprises:

passing, by the PHM module, the at least one first interpretable command and the at least some of the plurality of predictive learning model parameter values to the command interpreter module; and generating, by the command interpreter module based on the at least one first interpretable command and the at least some of the plurality of predictive learning model parameter values, the first executable bytecodes that invoke the first externally invokable function with the at least some of the plurality of predictive learning model parameter values; and wherein executing the first executable bytecodes to generate the notification identifying the predicted future condition of the first component for presentation on the display device further comprises:

invoking, by the first executable bytecodes, the first externally invokable function with the at least some of the plurality of predictive learning model parameter values; and generating the notification identifying the predicted future condition of the first component for presentation on the display device.

6. The method of claim 1, wherein the PHM module is written in a first programming language having a first syntax, and wherein the plurality of first interpretable commands is written in a second interpretable programming language having a second syntax that is different from the first syntax.

7. The method of claim 6, wherein the plurality of first interpretable commands comprises English language words.

8. The method of claim 1, wherein the predicted future condition of the first component comprises a remaining useful life (RUL) of the first component, and further comprising:

predicting, by the first executable bytecodes, based on the sensor data and the at least some of the plurality of predictive learning model parameter values, the RUL of the first component; and generating, by the first executable bytecodes, the notification for presentation on the display device that indicates the RUL of the first component.

9. The method of claim 8, further comprising:

receiving a second analytics script generated at a third time that is later than the second time, the second analytics script replacing the first analytics script, the second analytics script comprising a plurality of second interpretable commands and a plurality of updated predictive learning model parameter values associated with the first predictive learning model, some of the plurality of second interpretable commands configured to invoke some of the plurality of externally invokable functions with at least some of the plurality of updated predictive learning model parameter values;

invoking, by the PHM module, the command interpreter module to interpret at least one second interpretable command of the plurality of second interpretable commands and the at least some of the plurality of updated predictive learning model parameter values to generate second executable bytecodes;

executing the second executable bytecodes;

predicting, by the second executable bytecodes, based on the sensor data and the at least some of the plurality of updated predictive learning model parameter values, an updated RUL of the first component that is different from the RUL; and generating, by the second executable bytecodes, a notification for presentation on the display device that indicates the updated RUL of the first component.

10. The method of claim 9, wherein the first component comprises one of a fuel pump and an alternator.

11. The method of claim 1, further comprising:

processing, by the PHM module, the first analytics script; and assigning, by the PHM module based on the first analytics script, each corresponding sensor of the plurality of corresponding sensors a corresponding port value, and wherein the plurality of first interpretable commands is configured to access the sensor data associated with each corresponding sensor based on the corresponding port value.

12. The method of claim 1, wherein receiving the first analytics script generated at the second time comprises:

interfacing with a remote device; and receiving the first analytics script generated at the second time from the remote device.

13. A prognostics health management (PHM) system for implementing PHM on a machine having a plurality of components, comprising:

a sensor interface configured to be coupled to a plurality of sensors;

a communication interface configured to communicate with a remote device;

a controller comprising a processor coupled to the sensor interface and the communication interface, and configured to:

generate sensor data that quantifies real-time conditions of the plurality of components based on sensor signals generated by a plurality of corresponding sensors;

load a PHM module generated at a first time and implementing a plurality of externally invokable functions;

receive a first analytics script generated at a second time, the first analytics script comprising a plurality of first interpretable commands and a plurality of predictive learning model parameter values associated with a first predictive learning model, some of the plurality of first interpretable commands configured to invoke some of the plurality of externally invokable functions with at least some of the plurality of predictive learning model parameter values; and invoke, via the PHM module, a command interpreter module to interpret at least one first interpretable command of the plurality of first interpretable commands and the at least some of the plurality of predictive learning model parameter values and generate first executable bytecodes based on the at least one first interpretable command and the at least some of the plurality of predictive learning model parameter values, the first executable bytecodes configured to invoke the at least some of the plurality of externally invokable functions with the at least some of the plurality of predictive learning model parameter values identified in the at least one first interpretable command; and execute the first executable bytecodes to generate a notification identifying a predicted future condition of a first component for presentation on a display device based at least in part on at least some of the plurality of predictive learning model parameter values and the sensor data that quantifies the real-time condition of the first component.

14. The PHM system of claim 13, wherein to generate the sensor data that quantifies the real-time conditions of the corresponding components based on sensor signals generated by the plurality of corresponding sensors, the controller is further configured to:
receive, by the PHM system, the plurality of sensor signals generated by the plurality of corresponding sensors, the plurality of sensor signals indicating the real-time conditions of the plurality of components; and
process the plurality of sensor signals to generate the sensor data that quantifies the real-time conditions of the plurality of components.

15. The PHM system of claim 14, wherein to process the sensor signals to generate the sensor data that quantifies the real-time conditions of the plurality of components, the controller is further configured to filter the sensor signals and extract features from the sensor signals to generate the sensor data.

16. The PHM system of claim 13, wherein the controller is further configured to:
detect, by the PHM module, the at least one first interpretable command in the first analytics script, the at least one first interpretable command configured to invoke a first externally invokable function of the plurality of externally invokable functions with the at least some of the plurality of predictive learning model parameter values; and
wherein to invoke the command interpreter module to interpret the at least one first interpretable command and generate the first executable bytecodes, the controller is further configured to:
pass, by the PHM module, the at least one first interpretable command and the at least some of the plurality of predictive learning model parameter values to the command interpreter module; and
generate, by the command interpreter module based on the at least one first interpretable command and the at least some of the plurality of predictive learning model parameter values, the first executable bytecodes that invoke the first externally invokable function with the at least some of the plurality of predictive learning model parameter values; and
wherein to execute the first executable bytecodes to generate the notification identifying the predicted future condition of the first component for presentation on the display device, the controller is further configured to:
invoke, by the first executable bytecodes, the first externally invokable function with the at least some of the plurality of predictive learning model parameter values; and
generate the notification identifying the predicted future condition of the first component for presentation on the display device.

17. The PHM system of claim 13, wherein the PHM module is written in a first programming language having a first syntax, and wherein the plurality of first interpretable commands is written in a second interpretable programming language having a second syntax that is different from the first syntax.

18. The PHM system of claim 17, wherein the plurality of first interpretable commands comprises English language words.

19. The PHM system of claim 13, wherein the first component comprises one of a fuel pump and an alternator.

20. A method for implementing prognostic health management (PHM) on a machine, comprising:
receiving, by a PHM system comprising a processor, a plurality of sensor signals from a plurality of corresponding sensors, the plurality of sensor signals being indicative of real-time conditions of a plurality of components;
accessing, by a PHM module implementing a plurality of externally invokable functions, a first analytics script generated at a point in time, the first analytics script comprising a plurality of first interpretable commands and a plurality of predictive learning model parameter values associated with a first predictive learning model, some of the plurality of first interpretable commands configured to invoke some of the plurality of externally invokable functions; and
in response to a real-time condition of a first component of the plurality of components, interpreting, by the PHM module, a respective first interpretable command and generating respective first executable bytecodes based on the respective first interpretable command, and causing execution of the respective first executable bytecodes to generate a notification identifying a predicted future condition of the first component for presentation on a display device based at least in part on at least some of the plurality of predictive learning model parameter values and the real-time condition of the first component.

* * * * *